United States Patent [19]
Ries et al.

[11] Patent Number: 5,952,517
[45] Date of Patent: Sep. 14, 1999

[54] METHOD FOR PREPARING CLEAVED PRODUCTS FROM CASTOR OIL OR DERIVATIVES THEREOF

[75] Inventors: Charles David Ries, Maplewood; Thomas Samuel Totah, Plainsboro, both of N.J.

[73] Assignee: Caschem, Inc., Bayonne, N.J.

[21] Appl. No.: 08/800,416

[22] Filed: Feb. 14, 1997

[51] Int. Cl.⁶ .................................................. C07B 33/00
[52] U.S. Cl. ............................................................ 554/132
[58] Field of Search ............................................. 554/132

[56] References Cited

PUBLICATIONS

Vasishtha et al., JAOCS., vol. 67, No. 5, pp. 333–337, May 1990.

*Primary Examiner*—Gary Geist
*Assistant Examiner*—Deborah D Carr
*Attorney, Agent, or Firm*—Pennie & Edmonds LLP

[57] ABSTRACT

A process for producing a cleaved product from castor oil, or derivatives thereof, by high temperature caustic oxidation reaction accomplished by combining at least one chemically inert heat transfer fluid, a catalyst, and an alkali in aqueous solution to form a first mixture wherein the diluent is present in an amount sufficient to reduce foaming and solidification of the mixture while increasing the yield and improving the purity and adding a ricinic compound to the first mixture to form a second mixture. The temperature of the second mixture is raised to a level sufficient to conduct pyrolysis, and the cleaved product produced thereby is recovered by adding an acid to the reaction mixture in an amount sufficient to acidify the reaction mixture down below a pH of about 6. The invention further relates to the reaction mixture used to produce the cleaved products. The present invention provides higher product yields and purer cleaved products produced by the oxidation of castor oil or its derivatives than conventionally obtained.

26 Claims, No Drawings

METHOD FOR PREPARING CLEAVED PRODUCTS FROM CASTOR OIL OR DERIVATIVES THEREOF

FIELD OF THE INVENTION

The present invention relates to a process and reaction mixture for producing a cleaved product from castor oil or derivatives thereof by high temperature oxidation of a mixture of a ricinic compound, a catalyst, an alkali in aqueous solution, and a heat transfer fluid in an amount sufficient to reduce foaming and solidification of the reaction mixture while increasing the yield and improving the purity.

BACKGROUND OF THE INVENTION

The cleaved products of castor oil and its derivatives have several useful applications. For example, one cleaved product, sodium sebacate, is a precursor to sebacic acid. Sebacic acid is extremely valuable in the production of nylon 610 and alkyds. Unfortunately, complications associated with the commercial production of such cleaved products often make the process costly and wasteful.

Presently, these cleaved products are generally produced by the high temperature caustic oxidation of castor oil in the presence of a strong alkali and a catalyst. Several problems plague this production method. First, when the castor oil or derivative is treated with alkali or caustic, the reaction mixture has a tendency to foam violently and/or the reactants tend to solidify. These complications typically hinder, or even stop, the ongoing oxidation reaction. Furthermore, the hard alkaline soap formed when the reactants solidify poses additional problems, since it is a poor conductor of heat and makes the reactants difficult to mix by mechanical agitation.

There exist alternative methods of producing such cleaved products, but they are often hampered by high production costs. Certain references which disclose the production of cleaved products of castor oil and its derivatives are discussed below.

U.S. Pat. No. 4,786,666 discloses a process for making epoxy esters from epoxy resins and fatty acids, wherein the epoxy resin is made from a diglycidyl ether of a dihydric phenol and castor oil polyglycidyl ether reacted with a dihydric phenol. The castor oil polyglycidyl ether is prepared by reacting castor oil and epichlorohydrin using a Lewis acid catalyst and dihydrohalogenating the chlorohydrin adduct with a caustic agent.

U.S. Pat. No. 4,574,053 discloses a soap bar filled with particulate inorganic filler materials that are coated with fatty acid that has chemically reacted with the filler. The fatty acid used in the soap base may be castor oil.

U.S. Pat. No. 4,299,976 discloses a process for producing an unsaturated diester useful as a precursor for sebacic acid, which is produced by contacting methyl penta-2,4-dienoate at 30 to 150° C. under an inert atmosphere with a catalytic amount of a homogeneous palladium complex. This patent also discloses several processes for preparing sebacic acid, including an existing commercial process using castor oil. That process is accomplished by caustic decomposition of ricinoleic acid at 245° C. to yield disodium sebacate acid, followed by hydrolysis of the disodium sebacate, to produce sebacic acid.

U.S. Pat. No. 4,298,737 discloses the synthesis of piperidinyl substituted 1,4-diaza-2-cycloalkanones and substituted derivatives thereof by combining a piperidinyl substituted diamine and a suitable co-reactant in the presence of a phase transfer catalyst and caustic, for use as UV stabilizers in photodegradable plastics. The caustic agent retards formation of the desired product and thereby helps control the exothermic reaction. Castor oil may be added to the stabilized polymer as an optional ingredient.

U.S. Pat. No. 4,251,451 discloses a process for reacting a mixture of branched and linear alcohols with a caustic to produce a reaction mixture containing carboxylic acid salts and to liberate hydrogen by adding an inert diluent that reduces the tendency of the reaction mixture to foam and solidify. Sufficient diluent is added at a particular time in the reaction, before hydrogen release but after the reaction has begun, to inhibit foam formation and solidification of the reaction mixture, while maintaining fluidity of the reaction mixture to allow passage of liberated hydrogen. Furthermore, this reference does not disclose the use of the recited process in the oxidation of castor oil or its derivatives.

U.S. Pat. No. 3,671,581 discloses a process for the production of carboxylic acids by reacting a starting material, one of which is the non-acidic by-product obtained from the oxidation of castor oil to produce sebacic acid, with fused alkali metal hydroxide at a temperature of between 250 to 375° C.

U.S. Pat. No. 3,668,092 discloses a process for bleaching carboxylic acid esters, such as castor oil, or epoxy compounds, by irradiating them with UV light in the presence of a peroxy compound. A similar prior process involved treatment with a caustic.

None of these references disclose how to reduce the foaming and/or solidification that has hindered the previous oxidation of castor oil and/or derivatives thereof. It would be desirable to produce cleaved products of castor oil and or its derivatives while reducing the foaming and/or solidification to raise product yield and purity.

SUMMARY OF INVENTION

The invention relates to a process for producing a cleaved product from a ricinic compound by a high temperature caustic oxidation reaction. This is accomplished by combining at least one diluent, a catalyst, and an alkali in aqueous solution to form a first mixture, wherein the diluent is present in an amount sufficient to reduce foaming and solidification of the reaction mixture while increasing the yield and improving the purity, adding a ricinic compound to the first mixture to form a second mixture, and raising the temperature of the second mixture to a level sufficient to initiate a pyrolysis reaction and form a cleaved product from the ricinic compound.

In a preferred embodiment, the ricinic compound is castor oil, a ricinoleate, a ricinic acid ester, a ricinoleic acid, a ricinoleic acid amide, a ricinoleic acid ester, a sulfonated ricinoleate, a ricinic ester, a ricinic alcohol, a ricinoleyl acid, a ricinoleyl acid amide, a ricinoleyl alcohol, a ricinoleyl alcohol ester, an alkali ricinoleate or a mixture thereof. In a more preferred embodiment, the ricinic compound is glycerol triricinoleate, glyceryl tri-(12-acetyl ricinoleate), glyceryl tri(12-hydroxystearate), glyceryl tri-(12-acetoxystearate), turkey red oil, methylated ricinoleate, methyl ricinoleate, capryl ricinoleate, proylene glycol ricinoleate or a mixture thereof.

In one embodiment, the process further includes adding an acid to the second mixture in an amount sufficient to cause separation of the heat transfer fluid and the cleaved product. In another embodiment, the process further includes adding an acid to the cleaved product in an amount sufficient to convert the cleaved product into a free acid. In yet another embodiment, the reaction mixture is agitated before adding the ricinic compound.

In a preferred embodiment, the ricinic compound is added to the first mixture after the temperature of the first mixture reaches a level sufficient to conduct a pyrolysis reaction, thereby initiating the reaction and generating the cleaved product. In another preferred embodiment, the heat transfer fluid possesses oxidative stability. In yet another preferred embodiment, the heat transfer fluid is a derivative of an aromatic oil, a glycol oil, a petroleum oil, a fluorocarbon oil, and/or a silicone oil. In another preferred embodiment, the reaction temperature is raised to about 250° C. to 320° C. In another preferred embodiment, the alkali has a pH greater than about 9, while in yet another, the alkali comprises sodium hydroxide. In another embodiment, the process occurs at about atmospheric pressure.

In a preferred embodiment, the cleaved product is hendecenoic acid, undecenoic acid, undecylenic acid, 10-hydroxydecanoic acid, 2-octanol, 2-octanone (methyl hexy ketone), octene, heptanoic acid, nonanoic acid, myristic acid, palmitic acid, hydroxydecanoic-sebacic ester, sodium sebacate, or hydroxydecanoic esters. In another preferred embodiment, the catalyst is a nitrate. In yet another preferred embodiment, the free acid is sebacic acid.

The invention further relates to a reaction mixture for producing a cleaved product from castor oil or its derivatives by high temperature oxidation by combining a ricinic compound, an alkali in aqueous solution, a catalyst, and a chemically inert heat transfer fluid in an amount sufficient to reduce foaming and solidification of the reaction mixture while increasing the yield and improving the purity.

In a preferred embodiment, the heat transfer fluid possesses oxidative stability. In another embodiment, the reaction occurs at about atmospheric pressure. In a more preferred embodiment, the heat transfer fluid is a derived from an aromatic oil, a glycol oil, a petroleum oil, a fluorocarbon oil, and/or a silicone oil.

In a preferred embodiment of the invention, the reaction temperature of the reaction is about 250° C. to 320° C. In another preferred embodiment, the alkali has a pH greater than about 9. In a more preferred embodiment, the alkali includes sodium hydroxide.

In another preferred embodiment, the ricinic compound is castor oil, a ricinoleate, a ricinic acid ester, a ricinoleic acid, a ricinoleic acid amide, a ricinoleic acid ester, a sulfonated ricinoleate, a ricinic ester, a ricinic alcohol, a ricinoleyl acid, a ricinoleyl acid amide, a ricinoleyl alcohol, a ricinoleyl alcohol ester, an alkali ricinoleate or a mixture thereof. In a more preferred embodiment, the ricinic compound is glycerol triricinoleate, glyceryl tri-(12-acetyl ricinoleate), glyceryl tri(12-hydroxystearate), glyceryl tri-(12-acetoxystearate), turkey red oil, methylated ricinoleate, castor oil, methyl ricinoleate, capryl ricinoleate, proylene glycol ricinoleate or a mixture thereof.

In one preferred embodiment, the cleaved products are hendecenoic acid, undecenoic acid, undecylenic acid, 10-hydroxydecanoic acid, 2-octanol, 2-octanone (methyl hexy ketone), octene, heptanoic acid, nonanoic acid, myristic acid, palmitic acid, hydroxydecanoic-sebacic ester, sodium sebacate, or hydroxydecanoic esters. In one preferred embodiment, the catalyst is a nitrate, and in a more preferred embodiment, the catalyst is sodium nitrate.

DETAILED DESCRIPTION OF THE INVENTION

Diluents, such as heat transfer fluids, advantageously reduce the violent foaming and/or solidification of reactants that occurs during the caustic oxidation of castor oil and its derivatives. Heat transfer fluids are normally used in closed-loop pressurized external heat transfer systems. Yet, the ability of heat transfer fluids to provide uniform heating allows them to mitigate the violent foaming and solidification of reactants that typically occurs during the caustic oxidation of castor oil or its derivatives. In addition, the chemical inertness, low volatility, and resistance to fluid breakdown of heat transfer fluids makes them useful diluents in the present reaction.

This invention provides a method of preparing cleaved products, such as hendecenoic acid, undecenoic acid, undecylenic acid, 10-hydroxydecanoic acid, 2-octanol, 2-octanone (methyl hexy ketone), octene, heptanoic acid, nonanoic acid, myristic acid, palmitic acid, hydroxydecanoic-sebacic ester, sodium sebacate, or hydroxydecanoic esters from castor oil or its derivatives by high temperature oxidation in the presence of an alkali, a catalyst, and at least one chemically inert heat transfer fluid. The use of heat transfer fluids advantageously facilitates more even heating of the reaction solution, while reducing violent foaming and formation of rigid masses of reactants typically found in conventional oxidation reactions of this kind. Furthermore, heat transfer fluids are typically non-hazardous, non-toxic and often are not subject to EPA regulations, which tends to make them inexpensive to purchase and handle. The heat transfer fluids used in the invention are chemically inert and, therefore, do not react with the reactor walls or seals, and they can be recycled to reduce costs and waste. Finally, the use of heat transfer fluids reduces the formation of high fouling abrasive coke that may coat the heated reactor surface. Thus, the use of a heat transfer fluid for producing cleaved products of castor oil or its derivatives advantageously provides a more efficient process that yields more product having a higher purity.

The cleaved products are produced by first adding a diluent, such as a heat transfer fluid, to a reaction mixture of a catalyst and an alkali solution. The reaction mixture is then heated to a temperature at which the oxidation reaction, or pyrolysis, can be conducted. Then, castor oil or its derivatives are added to the reaction mixture, although they may be added prior to the heating of the reaction mixture. Once the desired cleaved product has been generated, the reaction solution may be cooled and acidified to separate the cleaved product from the undesired by-products and diluent.

In particular, the invention involves first charging effective amounts of a heat transfer fluid, a catalyst, and an aqueous solution of an alkali into a reactor suitable for a caustic oxidation reaction, such as a Parr reactor. Castor oil, its derivatives, or mixtures thereof, hereinafter referred to as "ricinic compounds," can also be added to the reaction mixture at this point. It is preferable, however to add the ricinic compound after the reaction mixture has been heated to a temperature sufficient to conduct the oxidation, or pyrolysis, reaction.

Preferably, the diluent is a heat transfer fluid; more preferably a heat transfer fluid derived from an aromatic oil, a glycol oil, a petroleum oil, a fluorocarbon oil, and/or a silicone oil; and most preferably a heat transfer fluid with oxidative stability. Preferred diluents for the reaction include the following: AMOLITE 11, AMOLITE 22, AMOLITE 32, AMOLITE 46, AMOLITE 68, AMOLITE 100, and HEAT TRANSFER No. 4199 all commercially available from Amolite Lubricants Inc., which conducts business at 200 East Randolph Street, Chicago, Ill. 60601; FOMBLIN YR1500, GALDEN HT-90, and GALDEN HT-270 all commercially available from Ausimont USA Inc., which has a principal place of business at 10 Leonards Lane, Thorofare, N.J. 08086-2150; CHEMTHERM 550, CHEMTHERM 650, CHEMTHERM 700, THERMALANE 600, and THERMALANE 800 all commercially available from Costal Chemical Co. Inc., which has a principal place of business at 3520 Veterans Memorial Drive, Abbeville, La. 70510-5708; DOWFROST, DOWFROST HD, DOWTHERM A, DOWTHERM G, DOWTHERM HT, DOWTHERM J, DOWTHERM Q, DOWTHERM SR-1, DOWTHERM 4000, SYLTHERM 800, SYLTHERM HF, and SYLTHERM XLT all commercially available from Dow Chemical Co., which conducts business at P.O. Box 2166, Midland, Mich. 48674-2166; CALORIA HT 43 commercially available from Exxon Co. USA, which conducts business at 225 East John Carpenter Freeway, Irving, Tex. 75062; MARLOTHERM LH, MARLOTHERM N, MARLOTHERM P1, MARLOTHERM P2, MARLOTHERM SH, and MARLOTHERM X all commercially available from Huls America Inc., which conducts business at P.O. Box 456, 80 Centennial Avenue, Piscataway, N.J. 08855-0456; MOBILTHERM Light and MOBILTHERM 603 commercially available from Mobil Oil Corp., which conducts business at 3225 Gallows Road, Fairfax, Va. 22037; THERMINOL 55, THERMINOL 59, THERMINOL 66, THERMINOL D12, THERMINOL VP1, and THERMINOL FS all commercially available from Monsanto Co., which conducts business at 800 North Lindbergh Boulevard, St. Louis, Mo. 63167; MULTITHERM PG-1, MULTITHERM IG-2, and MULTITHERM 503 all commercially available from MultiTherm Corp., which has a principal place of business at 125 South Front Street, Darby, Pa. 19023-2932; ULTRON SYNTHERM 700 commercially available from Pacer Lubricants Div., South Coast Terminals, which has a principal place of business at 7401 Wallisville Road, Houston, Tex. 77020-3555; PARATHERM NF and PARATHERM HE commercially available from Paratherm Corp., which has a principal place of business at 1050 Colwell Road, Conshohocken, Pa. 19428; CALFLO AF, CALFLO FG, CALFLO HTF, and CALFLO LT all commercially available from Petro-Canada, which has a principal place of business at 150 6 Avenue South West, Calgary, AB T2P 3Y; XCELTHERM MK1, XCELTHERM XT, XCELTHERM 550, and XCELTHERM 600 all commercially available from Radco Industries Inc., which has a principal place of business at 39w930 Midan Drive, Lafox, Ill. 60147; FLUORINART FC-40, FLUORINART FC-43, FLUORINART FC-70, FLUORINART FC-72, FLUORINART FC-77, FLUORINART FC-84, FLUORINART FC-87, FLUORINART FC-3283, FLUORINART FC-3284, and FLUORINART FC-5312 all commercially available from 3M Specialty Products, which conducts business at 420 Frontage Road, West Haven, Conn. 06516-4154; phenol, cresols, xylenols and the like, or a mixture thereof. CALFLO-HTF, CALFLO-AF, PARATHERM NF, MARLOTHERM SH, THERMINOL 66, phenol or m-Cresol, or a mixture thereof are examples of the most preferred heat transfer fluids. These heat transfer fluids are added in an amount sufficient to reduce foaming and solidification of the reaction mixture, while increasing the yield and improving the purity of the cleaved products.

The types and effective amounts of catalyst and alkali needed to conduct the oxidation of ricinic compounds are well known, and may be readily selected, by those skilled in the art. These characteristics are not essential to the invention. The catalysts are generally oxidation agents, such as bromates, chlorates, hypochlorites, perchlorates, peroxides, alkali metal nitrates, alkali permanganates, chromates, ferricyanides, areseniates, metal compounds, such as barium hydroxide, barium oxide, lead mono-oxide, lead di-oxide, lead sesqui-oxide, lead sub-oxide, red lead, cadmium oxide, cadmium hydroxide, zinc oxide, or zinc hydroxide. Sodium nitrate is the preferred catalyst, because of its oxidizing strength and homogeneity. Any alkali solution may be used, although it is preferable that the alkali creates a pH greater than about 9, more preferable that the alkali is an alkali metal hydroxide, and most preferable that the alkali is sodium hydroxide.

The amount of ricinic compound necessary to conduct the reaction is well known to those of ordinary skill in the art, and is not an essential component of the invention. Any ricinic compound is suitable for use in the present invention. Preferably, the ricinic compounds are castor oil, ricinoleate, ricinic acid ester, ricinoleic acid, ricinoleic acid amide, ricinoleic acid esters, sulfonated ricinoleate, ricinic ester, ricinic alcohol, ricinoleyl acid, ricinoleyl acid amide, ricinoleyl alcohol, ricinoleyl alcohol ester, alkali ricinoleate, ricinic alcohols, or a mixture thereof may be used in the reaction. The alkali ricinoleate may be salts of alkali or alkaline earth metals, such as sodium, potassium, lithium, calcium and barium, and the like, or a mixture thereof, may be used in the present reaction. Specifically, the more preferred ricinic compounds for the present reaction are glycerol triricinoleate, glyceryl tri-(12-acetyl ricinoleate), glyceryl tri(12-hydroxystearate), glyceryl tri-(12-acetoxystearate), turkey red oil, methylated ricinoleate, castor oil, methyl ricinoleate, capryl ricinoleate, proylene glycol ricinoleate, or a mixture thereof. Ricinoleic acid, methylated ricinoleate, and castor oil are the most preferred ricinic compounds used in the present invention.

After the reaction mixture is formed, the temperature of the reaction mixture is increased to a level sufficient to conduct the pyrolysis reaction. The oxidation, or pyrolysis, reaction may be conducted at temperatures ranging from about 200° C. up to the temperature at which appreciable decomposition of the reactants or reaction products would occur. Preferably, the reaction is conducted at temperatures between about 235° C. to 350° C. and, most preferably, at temperatures between about 250° C. to 320° C. The ricinic compound, of the type and an amount as discussed above, is preferably added to the reaction mixture once the temperature of the reaction is within the stated ranges, although it may be added prior to the heating of the reaction mixture.

The reaction mixture is maintained at the same temperature for a period of time, usually about 2 to 3 hours, after which the mixture is diluted with water. The exact reaction time is not essential, but is known to those of skill in the art and should be sufficient for the reaction to produce at least some cleaved product. The reaction is conducted at a pressure sufficient to permit the volatile by-products of the reaction to be condensed and collected. Preferably, the reaction is conducted at atmospheric pressure. Then, an acid, preferably a solution of sulfuric or hydrochloric acid, more preferably about 45–55 weight percent solution of sulfuric acid, is added to the mixture until a three-phase split occurs. This happens when the pH of the solution decreases to about 6 to 6.5. The top layer of the three-phase split contains the heat transfer fluid, which may be separated out for possible reuse. The middle layer, which contains undesired by-products of the reaction such as fatty acids or fatty impurities, is also separated out for possible use in other processes. Only the bottom layer of the three-phase split, which contains a preponderance of the desired cleaved product, is retained. Desired cleaved products include, but are not limited to, hendecenoic acid, undecenoic acid, undecylenic acid, 10-hydroxydecanoic acid, 2-octanol, 2-octanone (methyl hexy ketone), octene, heptanoic acid, nonanoic acid, myristic acid, palmitic acid, hydroxydecanoic-sebacic ester, sodium sebacate, or hydroxydecanoic esters. The bottom layer may be further acidified to a pH of about 2 to convert the cleaved product into a free acid, such as sebacic acid.

EXAMPLES

The following examples are provided to illustrate the present invention and are not to be considered limiting. All percentages are to be understood as percent by weight unless otherwise indicated.

Examples 1–6

Tests were conducted using various diluents to evaluate the resulting yield and purity when synthesizing sebacic acid. The following diluents were used in the screening design:

| Name | Company |
| --- | --- |
| THERMINOL 66 | Monsanto |
| PARATHERM NF | Paratherm Corporation |
| MARLOTHERM SH | Huls America |
| CALFLO-HTF | Petro-Canada |
| CALFLO-AF | Petro-Canada |
| m-cresol | EM Science |

Each of the tests was done in triplicate to eliminate anomalies. The purity of the resulting sebacic acid was determined by gas-liquid chromatography.

The data and results from these tests indicate no statistical difference between the diluents and runs when measuring the yield and purity of sebacic acid. Although m-Cresol produced a smaller standard deviation for yield and purity than the other heat transfer fluids, it is not as environmentally friendly as some of the other heat transfer fluids used in the screening example.

Example 1—THERMINOL 66

A 2 liter Parr reactor was charged with 43.4 grams of THERMINOL 66, 126.0 grams of 50 percent by weight sodium hydroxide, 15.6 grams of sodium nitrate, 34.3 grams of water, and 125.9 grams of ricinoleic acid. The heterogeneous mixture was heated to 280° C. and maintained at that temperature for 2 hours. The reaction mass was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The crude sebacic acid was recovered by filtration and vacuum dried at 105° C. for 12 hours. The results are as follows:

| Run | Yield % | Purity % C10 dibasic |
| --- | --- | --- |
| 1 | 94.4 | 48 |
| 2 | 75.0 | 67.7 |
| 3 | 71.3 | 79.9 |
| Average | 80.2 +/− 12.4 | 65.2 +/− 16.1 |

Example 2—PARATHERM NF

A 2 liter Parr reactor was charged with 43.4 grams of PARATHERM NF, 126.0 grams of 50 percent by weight sodium hydroxide, 15.6 grams of sodium nitrate, 34.3 grams of water, and 125.9 grams of ricinoleic acid. The heterogeneous mixture was heated to 280° C. and maintained at that temperature for 2 hours. The reaction mass was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The crude sebacic acid was recovered by filtration and vacuum dried at 105° C. for 12 hours. The results are as follows:

| Run | Yield % | Purity % C10 dibasic |
| --- | --- | --- |
| 1 | 80.3 | 71.8 |
| 2 | 78.3 | 74.7 |
| 3 | 59.7 | 86.0 |
| Average | 72.8 +/− 11.4 | 77.5 +/− 7.5 |

Example 3—MARLOTHERM SH

A 2 liter Parr reactor was charged with 43.4 grams of MARLOTHERM SH, 126.0 grams of 50 percent by weight sodium hydroxide, 15.6 grams of sodium nitrate, 34.3 grams of water, and 125.9 grams of ricinoleic acid. The heterogeneous mixture was heated to 280° C. and maintained at that temperature for 2 hours. The reaction mass was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The crude sebacic acid was recovered by filtration and vacuum dried at 105° C. for 12 hours. The results are as follows:

| Run | Yield % | Purity % C10 dibasic |
| --- | --- | --- |
| 1 | 63.9 | 75.1 |
| 2 | 42.6 | 84.3 |
| 3 | 57.3 | 83.8 |
| Average | 54.6 +/− 10.9 | 81.1 +/− 5.2 |

Example 4—CALFLO-HTF

A 2 liter Parr reactor was charged with 43.4 grams of CALFLO-HTF, 126.0 grams of 50 percent by weight sodium hydroxide, 15.6 grams of sodium nitrate, 34.3 grams of water, and 125.9 grams of ricinoleic acid. The heterogeneous mixture was heated to 280° C. and maintained at that temperature for 2 hours. The reaction mass was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The crude sebacic acid was recovered by filtration and vacuum dried at 105° C. for 12 hours. The results are as follows:

| Run | Yield % | Purity % C10 dibasic |
| --- | --- | --- |
| 1 | 70.2 | 62.3 |
| 2 | 46.0 | 92.8 |
| 3 | 65.9 | 85.8 |
| Average | 60.7 +/− 12.9 | 80.3 +/− 16.0 |

Example 5—CALFLO-AF

A 2 liter Parr reactor was charged with 43.4 grams of CALFLO-AF, 126.0 grams of 50 percent by weight sodium hydroxide, 15.6 grams of sodium nitrate, 34.3 grams of water, and 125.9 grams of ricinoleic acid. The heterogeneous mixture was heated to 280° C. and maintained at that temperature for 2 hours. The reaction mass was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The crude sebacic acid was recovered by filtration and vacuum dried at 105° C. for 12 hours. The results are as follows:

| Run | Yield % | Purity % C10 dibasic |
| --- | --- | --- |
| 1 | 97.1 | 69.6 |
| 2 | 70.2 | 86.2 |
| 3 | 63.7 | 85.1 |
| Average | 77.0 +/− 17.7 | 80.3 +/− 9.3 |

Example 6—m-Cresol

A 2 liter Parr reactor was charged with 43.4 grams of m-Cresol, an aqueous solution of 126.0 grams of 50 percent by weight sodium hydroxide, 15.6 grams of sodium nitrate, 34.3 grams of water, and 125.9 grams of ricinoleic acid. The heterogeneous mixture was heated to 280° C. and maintained at that temperature for 2 hours. The reaction mass was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The crude sebacic acid was recovered by filtration and vacuum dried at 105° C. for 12 hours. The results are as follows:

| Run | Yield % | Purity % C10 dibasic |
| --- | --- | --- |
| 1 | 70.8 | 88.2 |
| 2 | 74.3 | 90.7 |
| 3 | 74.9 | 87.2 |
| Average | 73.3 +/− 2.2 | 88.7 +/− 1.8 |

Examples 7–9

After the screening design, the process was optimized using a response surface design. The purpose of this set of tests was to examine the strength of the response surface model using castor oil and some of its derivatives. Each of these tests was duplicated to eliminate anomalies. The purity of the resulting sebacic acid was tested using gas-liquid chromatography. As a result of these tests, it was determined that the variability among the feedstock is greater than the variability among the runs. The results suggest that switching the feedstock will effect the yield, but not the purity.

Example 7—Methyl Ricinoleate

A 2 liter Parr reactor was charged with 960.1 grams of CALFLO-AF. A 50 percent by weight aqueous solution of 109.2 grams of sodium hydroxide was added while heating and stirring to obtain a uniform dispersion in the heat transfer fluid. The temperature of the heat transfer fluid and alkali mixture was heated to 285° C. A mixture of 807 grams of sodium nitrate dissolved in 10 grams of water and 156.0 grams of methyl ricinoleate was added to the hot alkali solution over a 3 hour period. After the addition the reaction mass was stirred an additional 4.4 hours. The reaction mass was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The crude sebacic acid was recovered by filtration and vacuum dried at 105° C. for 12 hours. The results are as follows:

| Run | Yield % | Purity % C10 dibasic |
| --- | --- | --- |
| 1 | 67.6 | 95.3 |
| 2 | 65.9 | 95.7 |
| Average | 66.7 +/− 1.2 | 95.5 +/− 0.3 |

Example 8—Ricinoleic Acid

A 2 liter Parr reactor was charged with 960.0 grams of heat transfer fluid, CALFLO-AF. A 50 percent by weight aqueous solution of 103.8 grams of sodium hydroxide was added while heating and stirring to obtain a uniform dispersion in the heat transfer fluid. The temperature of the heat transfer fluid and alkali mixture was heated to 285° C. A mixture of 8.7 grams of sodium nitrate dissolved in 10 grams of water and 156.0 grams of methyl ricinoleic acid was added to the hot alkali solution over a 3 hour period. After the addition the reaction mass was stirred an additional 4.4 hours. The reaction was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The sebacic acid was recovered by filtration and vacuum dried at 105° C. for 12 hours. The results are as follows:

| Run | Yield % | Purity % C10 dibasic |
| --- | --- | --- |
| 1 | 77.5 | 95.9 |
| 2 | 75.0 | 96.1 |
| Average | 76.2 +/− 1.8 | 96.0 +/− 0.14 |

Example 9—Castor Oil

A 2 liter Parr reactor was charged with 960.0 grams of heat transfer fluid, CALFLO-AF. The heat transfer fluid was previously used in example 2. A 50 percent by weight aqueous solution of 84.2 grams of sodium hydroxide was added while heating and stirring to obtain a uniform dispersion in the heat transfer fluid. The temperature of the heat transfer fluid and alkali mixture was heated to 285° C. A mixture of 8.7 grams of sodium nitrate dissolved in 10 grams of water and 156.0 grams of castor oil was added to the hot alkali solution over a 3 hour period. After the addition the reaction mass was stirred an additional 4.4 hours. The reaction was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The sebacic acid was recovered by filtration and vacuum dried at 105° C. for 12 hours. The results are as follows:

| Run | Yield % | Purity % C10 dibasic |
|---|---|---|
| 1 | 69.1 | 96.0 |
| 2 | 71.1 | 95.5 |
| Average | 70.1 +/− 1.4 | 95.7 +/− 0.3 |

Examples 10–11

Lastly, these tests were conducted to examine the use of CALFLO-AF multiple times before experiencing heat transfer fluid degradation.

Example 10—Ricinoleic Acid Using Recycled Heat Transfer Fluid

Two runs were made using the recycled heat transfer fluid from Example 8. The purity of the resulting sebacic acid was tested using gas-liquid chromatography. This example demonstrated that the heat transfer fluid, CALFLO-AF, can be reused at least one more time under the present conditions without experiencing degradation.

Run #1

A 2 liter Parr reactor was charged with 960.0 grams of heat transfer fluid, CALFLO-AF, recycled from example 8. A 50 percent by weight aqueous solution of 103.8 grams of sodium hydroxide was added while heating and stirring to obtain a uniform dispersion in the heat transfer fluid. The temperature of the heat transfer fluid and alkali mixture was heated to 285° C. A mixture of 8.7 grams of sodium nitrate dissolved in 10 grams of water and 156.0 grams of methyl ricinoleate was added to the hot alkali solution over a 3 hour period. After the addition the reaction mass was stirred an additional 4.4 hours. The reaction was then diluted with 3.3 liters of 90° C. water. The alkaline solution was acidified to pH 6 with 50 percent by weight sulfuric acid. A three-phase split immediately occurred. The bottom aqueous phase was separated from the middle by-product layer and the top heat transfer fluid layer. The bottom phase was further acidified to pH 2.0 and cooled to 15–20° C. The sebacic acid was recovered by filtration and vacuum dried at 105° C. for 12 hours.

The above method yielded 81.7% of sebacic acid, with a purity of 96.2% C10 dibasic acid.

Run #2

The conditions are the same as above. Run #2 yielded 77.2% of sebacic acid, with a purity of 94.1% C10 dibasic acid.

Example 11—Calflo-AF

Two sets of ten runs were used in the recycle test of Calflo-AF. The test involved charging a 2 liter Parr reactor with 624 grams of virgin Calflo-AF and a 50% aqueous solution of 82.6 grams of sodium hydroxide. The temperature of the thermal fluid and alkali mixture was heated to 285° C. A mixture of 8.7 grams of sodium nitrate dissolved in 10 grams of water and 156 grams of ricinoleic acid was added to the hot alkali solution over a 3 hour period. After the addition the reaction mass was stirred an additional hour. The reaction was then diluted with 3.3 liters of 90° C. water. The alkaline solution was acidify to pH 6 to 6.5 with 50% sulfuric acid. A three phase split immediately occurred. The bottom aqueous phase was separated from the middle by-product layer and the top thermal by filtration, washed with an additional 2 liters of water, to remove residual sulfuric acid and sodium sulfate, and vacuum dried at 105° C. for 12 hours. The middle and top layer were reused as in the preceding runs. The average yield was based on a 95% confidence interval, and the purity was determined by gas-liquid chromatography. The yields and purities are as follows:

| Use | Yield % | Purity % |
|---|---|---|
| Set #1 | | |
| 1 | 73.8 | 95.1 |
| 2 | 73.4 | 95.7 |
| 3 | 80.6 | 95.5 |
| 4 | 82.8 | 95.2 |
| 5 | 76.4 | 95.5 |
| 6 | 77.6 | 94.8 |
| 7 | 76.6 | 94.5 |
| 8 | 74.3 | 94.7 |
| 9 | 69.4 | 94.9 |
| 10 | 71.2 | 94.6 |
| Average | 75.6 +/− 3.1 | 95.1 +/− 0.3 |
| Set #2 | | |
| 1 | 73.8 | 96.7 |
| 2 | 60.3 | 94.4 |
| 3 | 77.7 | 96.0 |
| 4 | 82.7 | 94.6 |
| 5 | 77.8 | 95.5 |
| 6 | 81.4 | 93.9 |
| 7 | 75.1 | 95.4 |
| 8 | 64.4 | 93.3 |
| 9 | 72.4 | 92.8 |
| 10 | 70.6 | 93.2 |
| Average | 73.6 +/− 5.4 | 94.6 +/− 1.0 |

Although preferred embodiments of the invention have been described in the foregoing Detailed Description of the Invention, it will be understood that the invention is not limited to the embodiments disclosed but is capable of numerous modifications without departing from the spirit and scope of the present invention. It will be understood that the chemical details may be slightly different or modified by one of ordinary skill in the art without departing from the methods and compositions disclosed and taught by the present invention.

What is claimed is:

1. A process for producing a cleaved product from a ricinic compound by a high temperature caustic oxidation reaction comprising:
    combining at least one diluent, a catalyst, and an alkali in aqueous solution to form a first mixture, wherein the diluent is a heat transfer fluid having oxidative stability that is present in an amount sufficient to reduce foaming and solidification of the reaction mixture while increasing the yield and improving the purity;

adding a ricinic compound to the first mixture to form a second mixture; and raising the temperature of the second mixture to a level sufficient to initiate a pyrolysis reaction and form a cleaved product from the ricinic compound.

2. The process of claim 1 wherein the ricinic compound is castor oil, a ricinoleate, a ricinic acid ester, a ricinoleic acid, a ricinoleic acid amide, a ricinoleic acid ester, a sulfonated ricinoleate, a ricinic ester, a ricinic alcohol, a ricinoleyl acid, a ricinoleyl acid amide, a ricinoleyl alcohol, a ricinoleyl alcohol ester, an alkali ricinoleate or a mixture thereof.

3. The process of claim 1 further comprising adding an acid to the second mixture in an amount sufficient to cause separation of the heat transfer fluid and the cleaved product.

4. The process of claim 1, wherein the ricinic compound is added to the first mixture after the temperature of the first mixture reaches a level sufficient to conduct a pyrolysis reaction, thereby initiating the reaction and generating the cleaved product.

5. The process of claim 1 further comprising adding an acid to the cleaved product in an amount sufficient to convert the cleaved product into a free acid.

6. The process of claim 1, wherein the reaction mixture is agitated before adding the ricinic compound.

7. The process of claim 1, wherein the heat transfer fluid is a derivative of an aromatic oil, a glycol oil, a petroleum oil, a fluorocarbon oil, and/or a silicone oil.

8. The process of claim 1, wherein the reaction temperature is raised to about 250° C. to 320° C.

9. The process of claim 1, wherein the alkali has a pH greater than about 9.

10. The process of claim 1, wherein the alkali comprises sodium hydroxide.

11. The process of claim 2, wherein said ricinic compound is glycerol triricinoleate, glyceryl tri-(12-acetyl ricinoleate), glyceryl tri(12-hydroxystearate), glyceryl tri-(12-acetoxystearate), turkey red oil, methylated ricinoleate, methyl ricinoleate, capryl ricinoleate, proylene glycol ricinoleate or a mixture thereof.

12. The process of claim 1, wherein the process occurs at about atmospheric pressure.

13. The process of claim 1, wherein the cleaved product is hendecenoic acid, undecenoic acid, undecylenic acid, 10-hydroxydecanoic acid, 2-octanol, 2-octanone (methyl hexy ketone), octene, heptanoic acid, nonanoic acid, myristic acid, palmitic acid, hydroxydecanoic-sebacic ester, sodium sebacate, or hydroxydecanoic esters.

14. The process of claim 1, wherein the catalyst is a nitrate.

15. The process of claim 5, wherein the free acid is sebacic acid.

16. A reaction mixture for producing a cleaved product from castor oil or derivatives thereof by high temperature oxidation comprising:

a ricinic compound;

an alkali in aqueous solution;

a catalyst; and a heat transfer fluid having oxidative stability that is present in an amount sufficient to reduce foaming and solidification of the reaction mixture while increasing the yield and improving the purity.

17. The reaction mixture of claim 16, wherein the heat transfer fluid is a derived from an aromatic oil, a glycol oil, a petroleum oil, a fluorocarbon oil, and/or a silicone oil.

18. The reaction mixture of claim 16, wherein the reaction temperature of the reaction is about 250° C. to 320° C.

19. The reaction mixture of claim 16, wherein the alkali has a pH greater than about 9.

20. The reaction mixture of claim 16, wherein the alkali comprises sodium hydroxide.

21. The reaction mixture of claim 16, wherein the ricinic compound is castor oil, a ricinoleate, a ricinic acid ester, a ricinoleic acid, a ricinoleic acid amide, a ricinoleic acid ester, a sulfonated ricinoleate, a ricinic ester, a ricinic alcohol, a ricinoleyl acid, a ricinoleyl acid amide, a ricinoleyl alcohol, a ricinoleyl alcohol ester, an alkali ricinoleate or a mixture thereof.

22. The reaction mixture of claim 21, wherein the ricinic compound is glycerol triricinoleate, glyceryl tri-(12-acetyl ricinoleate), glyceryl tri(12-hydroxystearate), glyceryl tri-(12-acetoxystearate), turkey red oil, methylated ricinoleate, castor oil, methyl ricinoleate, capryl ricinoleate, proylene glycol ricinoleate or a mixture thereof.

23. The reaction mixture of claim 16, wherein the reaction occurs at about atmospheric pressure.

24. The reaction mixture of claim 16, wherein the cleaved products are hendecenoic acid, undecenoic acid, undecylenic acid, 10-hydroxydecanoic acid, 2-octanol, 2-octanone (methyl hexy ketone), octene, heptanoic acid, nonanoic acid, myristic acid, palmitic acid, hydroxydecanoic-sebacic ester, sodium sebacate, or hydroxydecanoic esters.

25. The reaction mixture of claim 16, wherein the catalyst is a nitrate.

26. The reaction mixture of claim 16, wherein the catalyst is sodium nitrate.

* * * * *